United States Patent
Hulse et al.

(10) Patent No.: US 8,541,634 B2
(45) Date of Patent: Sep. 24, 2013

(54) AZEOTROPE-LIKE COMPOSITIONS OF (Z)-1-CHLORO-3,3,3-TRIFLUOROPROPENE AND HYDROGEN FLUORIDE

(71) Applicant: Honeywell International Inc., Morristown, NJ (US)

(72) Inventors: Ryan Hulse, Getzville, NY (US); Hang T Pham, Amherst, NY (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 13/740,972

(22) Filed: Jan. 14, 2013

(65) Prior Publication Data
US 2013/0131404 A1 May 23, 2013

Related U.S. Application Data

(62) Division of application No. 13/253,270, filed on Oct. 5, 2011, now Pat. No. 8,378,158.

(60) Provisional application No. 61/419,322, filed on Dec. 3, 2010.

(51) Int. Cl.
| | |
|---|---|
| C07C 17/383 | (2006.01) |
| C07C 17/08 | (2006.01) |
| C07C 17/38 | (2006.01) |
| B01F 1/00 | (2006.01) |
| B01D 3/36 | (2006.01) |
| C09K 3/00 | (2006.01) |
| C09K 5/04 | (2006.01) |
| C09K 3/30 | (2006.01) |
| C11D 17/00 | (2006.01) |

(52) U.S. Cl.
USPC ......... 570/178; 570/177; 570/180; 570/164; 570/161; 570/167; 570/170; 570/135; 570/156; 252/2; 252/71; 252/182.12; 510/177; 510/408; 510/412

(58) Field of Classification Search
USPC ........... 570/135, 156, 161, 164, 165, 166, 570/167, 170, 177, 178, 180; 252/2, 71, 252/182, 12; 510/177, 408, 412
See application file for complete search history.

(56) References Cited

U.S. PATENT DOCUMENTS

| | | | |
|---|---|---|---|
| 5,710,352 A | 1/1998 | Tung | |
| 6,013,846 A * | 1/2000 | Wismer et al. | ............... 570/180 |
| 6,111,150 A | 8/2000 | Sakyu et al. | |

(Continued)

FOREIGN PATENT DOCUMENTS

WO 2010111067 A1 9/2010

OTHER PUBLICATIONS

G. Morrison & M.O. McLinden ; (1993) "Azeotropy in refrigerant mixtures"; Source: International Journal of Refrigeration, vol. 16, No. 2, pp. 129-138.

(Continued)

*Primary Examiner* — Joseph D Anthony
(74) *Attorney, Agent, or Firm* — Bruce O. Bradford

(57) ABSTRACT

Disclosed are azeotropic and azeotrope-like mixtures of (Z)-1-chloro-3,3,3-trifluoropropene (1233zd(Z)) and hydrogen fluoride. Such compositions are useful as an intermediate in the production of 1233zd(Z). The latter compound is useful as a nontoxic, zero ozone depleting fluorocarbon useful as a solvent, blowing agent, refrigerant, cleaning agent, aerosol propellant, heat transfer medium, dielectric, fire extinguishing composition and power cycle working fluid.

8 Claims, 1 Drawing Sheet

Pressure versus composition measurements of 1233zd(Z) and HF at 0, 25 and 60°C

(56) References Cited

U.S. PATENT DOCUMENTS

| | | | |
|---|---|---|---|
| 6,362,383 B1 | 3/2002 | Wilmet et al. | |
| 6,472,573 B1* | 10/2002 | Yamamoto et al. | 570/164 |
| 6,528,691 B1 | 3/2003 | Elsheikh et al. | |
| 6,759,381 B1 | 7/2004 | Johnson et al. | |
| 6,844,475 B1 | 1/2005 | Tung et al. | |
| 6,858,762 B2* | 2/2005 | Baker et al. | 570/165 |
| 7,094,936 B1* | 8/2006 | Owens et al. | 570/257 |
| 7,183,448 B2* | 2/2007 | Nakada et al. | 570/164 |
| 7,829,747 B2 | 11/2010 | Wang et al. | |
| 7,833,433 B2 | 11/2010 | Singh et al. | |
| 8,075,797 B2* | 12/2011 | Hulse et al. | 252/67 |
| 2005/0101810 A1* | 5/2005 | Owens et al. | 570/227 |
| 2008/0207788 A1 | 8/2008 | Bowman et al. | |
| 2010/0237279 A1 | 9/2010 | Hulse et al. | |
| 2012/0010449 A1* | 1/2012 | Wismer et al. | 570/178 |
| 2012/0053369 A1* | 3/2012 | Hulse et al. | 570/135 |
| 2012/0184786 A1* | 7/2012 | Merkel et al. | 570/156 |
| 2012/0215039 A1* | 8/2012 | Hulse et al. | 570/160 |

OTHER PUBLICATIONS

Kim et al. ; (Mar. 1996) "A Study to Determine the Existence of an Azeotrpic R-22 "Drop-In" Substitute"; Source: Report from the Building Environment Division of the Building & Fire Research Laboratory of the U.S. Department of Commerce.

International Search Report & Written Opinion, issued Jun. 12, 2012, in counterpart International Patent Application No. PCT/US2011/062884.

* cited by examiner

Pressure versus composition measurements of 1233zd(Z) and HF at 0, 25 and 60°C
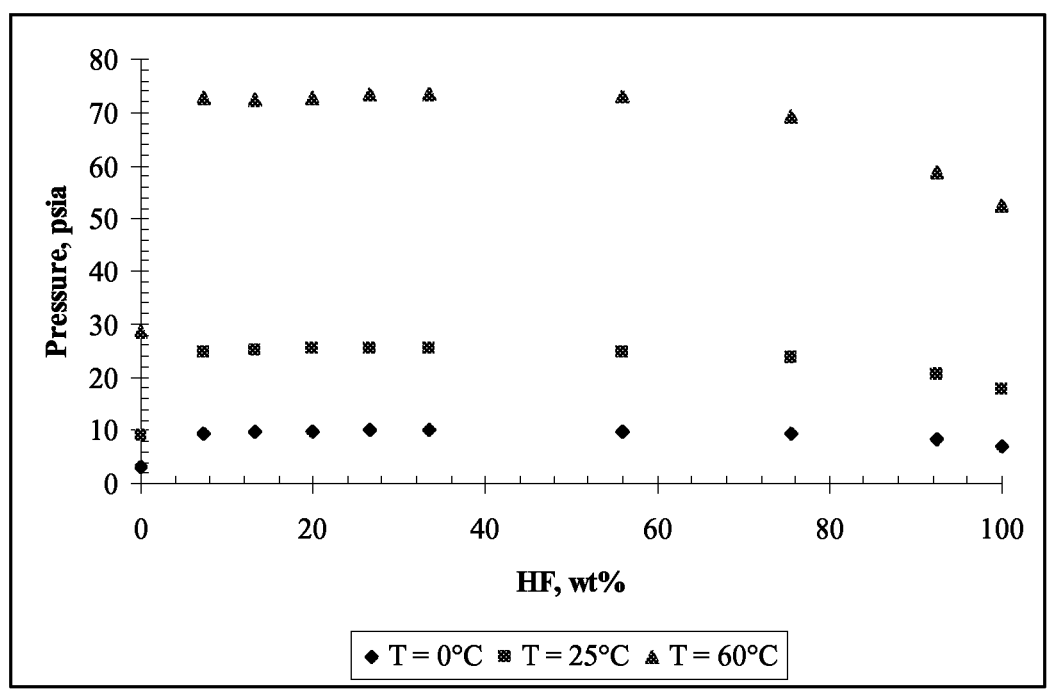

AZEOTROPE-LIKE COMPOSITIONS OF (Z)-1-CHLORO-3,3,3-TRIFLUOROPROPENE AND HYDROGEN FLUORIDE

CROSS-REFERENCE TO RELATED APPLICATIONS

This application is a divisional filing from commonly owned, U.S. application Ser. No. 13/253,270, filed Oct. 5, 2011, now U.S. Pat. No. 8,378,158. The '270 application claims domestic priority from commonly owned, U.S. Provisional Patent Application Ser. No. 61/419,322, filed Dec. 3, 2010. These documents are hereby incorporated herein by reference.

FIELD OF THE INVENTION

The present invention pertains to azeotropic and azeotrope-like compositions of (Z)-1-chloro-3,3,3-trifluoropropene (cis-1233zd or 1233zd(Z)) and hydrogen fluoride (HF).

BACKGROUND OF THE INVENTION

In recent years there has been some concern that some long lived fluorocarbons might be contributing, albeit in a small way, to global warming. Consequently, there is a worldwide effort to use fluorine-substituted hydrocarbons which have short atmospheric lifetime and therefore do not persist in the atmosphere. In this regard, (Z)-1-chloro-3,3,3-trifluoropropene (1233zd(Z)) having low global warming potential, is being considered as a replacement for some fluorocarbons such as 141b in solvents and as a blowing agent.

The production of 1223zd(Z) has been the subject of interest to provide an environmentally desirable product for use in blowing agents, refrigerants, cleaning agents, aerosol propellants, heat transfer media, dielectrics, fire extinguishing compositions and power cycle working fluids. It is known in the art to produce fluorocarbons such a 1233zd(Z) by reacting hydrogen fluoride with various hydrochlorocarbon compounds.

Because many CFCs are known to be ozone-depleting compounds, the use of these compounds has been curtailed in favor of chemicals that are more commercially acceptable. In some cases, alternate CFC compounds have been found to be both effective and more environmentally friendly.

As one example, 1-chloro-3,3,3-trifluoropropene (1233zd) has been found to have a wide variety of uses, for example as a heat transfer agent, as a foaming agent, and as a solvent, among other uses. See for example, U.S. Pat. No. 7,833,433, entitled "Heat Transfer Methods Using Heat Transfer Compositions Containing Trifluoromonochloropropene", U.S. Patent Publication No. 2008-0207788, entitled "Foaming Agents, Foamable Compositions, Foams and Articles Containing Fluorine Substituted Halogens, and Methods of Making the Same", and U.S. Pat. No. 6,362,383, entitled "Hydro-Fluorination of Chlorinated Hydrocarbons", which disclose examples of such uses.

The compound 1233zd may be produced by a number of different methods. See, for example, U.S. Pat. No. 7,829,747, entitled "Process for Dehydrofluorination of 3-chloro-1,1,1,3-tetrafluoropropane to 1-chloro-3,3,3-trifluoropropene"; U.S. Pat. No. 5,710,352, entitled "Vapor Phase Process for Making 1,1,1,3,3-pentafluoropropane and 1-chloro-3,3,3-trifluoropropane," U.S. Pat. No. 6,111,150, entitled "Method for Producing 1,1,1,3,3-pentafluoropropane," and U.S. Pat. No. 6,844,475, entitled "Low Temperature Production of 1-chloro-3,3,3-trifluoropropene (HCFC-1233zd)", which describe several methods for making 1233zd.

All of the documents cited above are hereby incorporated herein by reference in their entirety.

SUMMARY OF THE INVENTION

It has now been found that an important intermediate in the production of substantially pure 1233zd(Z), is an azeotrope or azeotrope-like mixture of 1233zd(Z) and hydrogen fluoride (HF). This binary intermediate, once formed, may thereafter be separated into its component parts by extraction or distillation techniques. The compound 1233zd(Z) has a boiling point of about 18° C. and HF has a boiling point of about 20° C. at standard atmospheric pressure. These azeotrope or azeotrope-like compositions find use not only as intermediates in the production of 1233zd(Z), but they are additionally useful as solvents and as compositions for removing surface oxidation from metals.

In addition, the formation of an azeotropic or azeotrope-like composition of 1233zd(Z) and HF is useful in separating a mixture of 1233zd(Z) and an impurity. When it is desired to separate a mixture of 1233zd(Z) and an impurity, HF is added to form an azeotropic mixture of 1233zd(Z) and HF, and then the impurity is removed from the azeotropic mixture, such as by distillation, scrubbing or other known means.

One embodiment of the invention provides an azeotropic composition consisting essentially of (Z)-1-chloro-3,3,3-trifluoropropene (1233zd(Z)) and hydrogen fluoride (HF).

Another embodiment of the invention provides an azeotropic or azeotrope-like composition which consists essentially of from about 1 to about 95 weight percent hydrogen fluoride and from about 5 to about 99 weight percent 1233zd(Z), which composition has a boiling point of about 0° C. to about 60° C. at a pressure of about 3 psia to a pressure of about 73 psia. In certain embodiments the composition consists of hydrogen fluoride and (Z)-1-chloro-3,3,3-trifluoropropene (1233zd(Z)). In certain embodiments, the hydrogen fluoride is present in an amount of from about 5 to about 90 weight percent. In certain embodiments, the hydrogen fluoride in present in an amount of from about 20 to about 35 weight percent. Certain embodiments of the invention have a boiling point of from about 0° C. to about 61° C. at a pressure of from about 3 psia to about 73 psia.

Another embodiment of the invention provides a method of forming an azeotropic or azeotrope-like composition which consists essentially of blending from about 1 to about 95 weight percent hydrogen fluoride and from about 5 to about 99 weight percent (Z)-1-chloro-3,3,3-trifluoropropene (1233zd(Z)), which composition has a boiling point of from about 0° C. to about 60° C. at a pressure of about 3 psia to about 73 psia. In certain embodiments the composition consists of hydrogen fluoride and (Z)-1-chloro-3,3,3-trifluoropropene (1233zd(Z)). In certain embodiments, the hydrogen fluoride is present in an amount of from about 5 to about 90 weight percent. In certain embodiments, the hydrogen fluoride in present in an amount of from about 20 to about 35 weight percent. In certain embodiments, the hydrogen fluoride is present in an amount of about 26±3 weight percent. In certain embodiments of the invention the composition has a boiling point of from about 0° C. to about 61° C. at a pressure of from about 3 psia to about 73 psia. In certain embodiments the composition has a boiling point of about 25° C. at a pressure of about 14.7 psia.

In certain embodiments, 1233zd(Z) can be isolated from the azeotropic like mixture of 1233zd(Z) and HF by extraction of HF. In certain embodiments, the extraction of HF is accomplished using water or other aqueous solutions. In certain embodiments, the extraction of HF is accomplished using sulfuric acid. In certain embodiments, the extraction of HF is accomplished by distillation, for example by extractive distillation, or pressure swing distillation.

The azeotropic and azeotrope-like mixtures of (Z)-1-chloro-3,3,3-trifluoropropene (1233zd(Z)) and hydrogen fluoride of the present invention are useful as an intermediate in the production of 1233zd(Z). This purified material is useful as a nontoxic, zero ozone depleting chlorofluorocarbon useful as a solvent, blowing agent, refrigerant, cleaning agent, aerosol propellant, heat transfer medium, dielectric, fire extinguishing composition and power cycle working fluid.

BRIEF DESCRIPTION OF THE DRAWING

FIG. 1 shows a plot of the vapor pressures of the mixtures formed in Example 1 as measured at 0° C., 25° C., and 60° C.

DETAILED DESCRIPTION OF THE INVENTION

The binary azeotrope of 1233zd(Z) and HF can be formed as described in the U.S. Pat. No. 7,829,747 where 244fa is dehydrofluorinated to yield 1233zd(Z), HF and other components such as (E)-1-chloro-3,3,3-trifluoropropene, hydrogen chloride, 1,3,3,3-tetrafluoropropene, 1,1,1,3,3-pentafluoropropane. Upon removal of the other compounds the binary azeotrope of 1233zd(Z) and HF remains.

1233zd(Z) forms azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope-like composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation.

One way to determine whether a candidate mixture is azeotrope-like within the meaning of this invention is to distill a sample of it under conditions which would be expected to separate the mixture into its separate components. If the mixture is a non-azeotrope or non-azeotrope-like, the mixture will fractionate, i.e., separate into its various components with the lowest boiling component distilling off first, and so on. If the mixture is azeotrope-like, some finite amount of the first distillation cut will be obtained which contains all of the mixture components and which is constant boiling or behaves like a single substance.

Another characteristic of azeotrope-like compositions is that there is a range of compositions containing the same components in varying proportions which are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique type of relationship but with a variable composition depending on the temperature and/or pressure. As is well known in the art, the boiling point of an azeotrope will vary with pressure.

As used herein, an azeotrope is a liquid mixture that exhibits a maximum or minimum boiling point relative to the boiling points of surrounding mixture compositions. An azeotrope or an azeotrope-like composition is an admixture of two or more different components which, when in liquid form under a given pressure, will boil at a substantially constant temperature, which temperature may be higher or lower than the boiling temperatures of the components and which will provide a vapor composition essentially identical to the liquid composition undergoing boiling.

For the purpose of this invention, azeotropic compositions are defined to include azeotrope-like compositions which means, a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of HF and 1233zd(Z) to form an azeotrope or azeotrope-like composition. By effective amount is meant an amount of each component which, when combined with the other component, results in the formation of an azeotrope or azeotrope-like mixture. The inventive compositions preferably are binary azeotropes which consist essentially of combinations of only HF with 1233zd(Z).

In the preferred embodiment, the inventive composition contains from about 1 to about 95 weight percent HF, preferably from about 5 weight percent to about 90 weight percent HF and most preferably from about 20 weight percent to about 35 weight percent HF. In the preferred embodiment, the inventive composition contains from about 5 to about 99 weight percent 1233zd(Z), preferably from about 10 weight percent to about 95 weight percent and most preferably from about 65 weight percent to about 80 weight percent. The composition of the present invention has a boiling point of about from 0° C. to about 60° C. at a pressure of about from 3 psia to about 73 psia. An azeotropic or azeotrope-like composition having about 26±3 weight percent HF and about 74±3 weight percent 1233zd(Z) has been found to boil at about 25° C. and 14.7 psia. The following non-limiting examples serve to illustrate the invention.

EXAMPLE 1

60 g of 1233zd(Z) were dissolved in 40 g of HF to form a heterogeneous azeotrope mixture. This experiment was conducted at 25° C., and at 14.6 psia.

EXAMPLE 2

Binary compositions containing solely 1233zd(Z) and HF are blended to form heterogeneous azeotrope mixtures at different compositions. The vapor pressures of the mixtures were measured at about 0°, 25° and 60° C. and the following results are noticed. Table 1 shows the vapor pressure measurement of 1233zd(Z) and HF as a function of composition of weight percent HF at constant temperatures of about 0°, 25°, and 61° C. The data show that 1233zd(Z) and HF formed a heterogeneous mixture.

TABLE 1

Pressure versus composition measurements of 1233zd(Z) and HF at 0°, 25° and 60° C.

| HF Wt % | T = 0° C. Press, psia | T = 25° C. Press, psia | T = 60° C. Press, psia |
|---|---|---|---|
| 0 | 3.2 | 8.9 | 28.5 |
| 7.3 | 9.3 | 24.6 | 72.8 |
| 13.4 | 9.7 | 25.2 | 72.4 |
| 20 | 9.9 | 25.5 | 72.7 |
| 26.7 | 10 | 25.5 | 73.4 |
| 33.4 | 10.1 | 25.5 | 73.4 |
| 56 | 9.7 | 24.6 | 73.2 |
| 75.5 | 9.3 | 23.8 | 69.2 |
| 92.4 | 8.2 | 20.5 | 58.8 |
| 100 | 6.9 | 17.8 | 52.4 |

These data also show that the mixture is an azeotrope since the vapor pressure of mixtures of 1233zd(Z) and HF is higher, at all indicated blend proportions, than 1233zd(Z) and HF alone, i.e., as indicated in the first and last rows when HF is 0 wt. % and 1233zd(Z) is at 100 wt. % as well as in the last row where 1233zd(Z) is at 0 wt. % and HF is at 100 wt. %. The data from Table 1 are also shown in graphic form in FIG. 1.

EXAMPLE 3

The azeotropic composition of the 1233zd(Z)/HF mixture is also verified by a Vapor-Liquid-Liquid equilibrium (VLLE) experiment. Here 66.6 g of 1233zd(Z) are dissolved in 33.4 g of HF to form a heterogeneous mixture (visual observation) at 26° C. The vapor composition, upper liquid (HF rich), and bottom liquid (organic) were sampled. The result shows that the azeotropic composition is about 26±3 wt % HF at 26° C.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A method of separating 1233zd(Z) from an azeotropic or azeotrope-like mixture, said mixture consists essentially of hydrogen fluoride and (Z)-1-chloro-3,3,3-trifluoropropene (1233zd(Z)), said mixture has a boiling point of from about 0° C. to about 60° C. at a pressure of from about 3 psia to about 73 psia, wherein the hydrogen fluoride is present in an amount of from about 20 to about 35 weight percent, said method comprising the step of extracting the HF from the mixture.

2. The method of claim 1, wherein the extraction of HF is accomplished using an aqueous solution.

3. The method of claim 2, wherein the aqueous solution is water.

4. The method of claim 1, wherein the extraction of HF is accomplished using sulfuric acid.

5. The method of claim 1, wherein the extraction of HF is accomplished by distillation.

6. The method of claim 5, wherein the distillation comprises extractive distillation.

7. The method of claim 5, wherein the distillation comprises pressure swing distillation.

8. The method of claim 1, wherein the mixture comprises hydrogen fluoride in an amount of about 26±3 weight percent.

* * * * *